United States Patent [19]

McClintock et al.

[11] Patent Number: 4,554,064
[45] Date of Patent: Nov. 19, 1985

[54] DUAL WORKING-ELECTRODE ELECTROCHEMICAL DETECTOR FOR HIGH PERFORMANCE LIQUID CHROMATOGRAPHY

[75] Inventors: Sam A. McClintock, Hudson; William C. Purdy, Montreal, both of Canada

[73] Assignee: Imasco-CDC Research Foundation, Toronto, Canada

[21] Appl. No.: 594,361

[22] Filed: Mar. 28, 1984

[51] Int. Cl.[4] .................... G01N 27/30; G01N 31/08
[52] U.S. Cl. ................. 204/411; 73/61.1 C; 422/70; 436/161
[58] Field of Search ............... 204/411, 412, 409; 73/61.1 C; 422/70; 436/161

[56] References Cited

PUBLICATIONS

G. W. Schieffer, Anal. Chem., 52, (1980), 1944.
W. A. MacCrehan and R. A. Durst, Anal. Chem., 53, (1981), 1700.
D. A. Roston and P. T. Kissinger, Anal. Chem., 54, (1982), 429.
M. Goto, T. Nakamura and D. Ishii, J. Chromatogr., 226, (1981), 33.
R. J. Fenn, S. Siggia and D. J. Curran, Anal. Chem, 50, (1978), 1067.
L. B. Anderson and C. N. Reilley, J. Electroanal Chem., 10, (1965), 295.
L. B. Anderson, C. N. Reilley, J. Electroanal. Chem., 10, (1965), 538.
Daryl A. Roston, Ronald E. Shoup and Peter T. Kissinger, Anal. Chem., 54, (1982), 1417 p. 1434.
S. A. McClintock and W. C. Purdy, Anal. Lett., 14, (1981), 791.

Primary Examiner—G. L. Kaplan
Attorney, Agent, or Firm—Bachman & LaPointe

[57] ABSTRACT

A dual working-electrode electrochemical detector includes two working-electrodes disposed in parallel, opposed and closely spaced relationship. The electrodes comprises a low temperature isotropic carbon, and the electrodes are spaced by a Teflon spacer. A channel is formed in the Teflon spacer for the flow of the biological fluid to be tested. The electrodes are mounted on hollow members, and the entire arrangement is held in fluid-tight engagement by a pair of yokes which overlie the hollow members.

6 Claims, 1 Drawing Figure

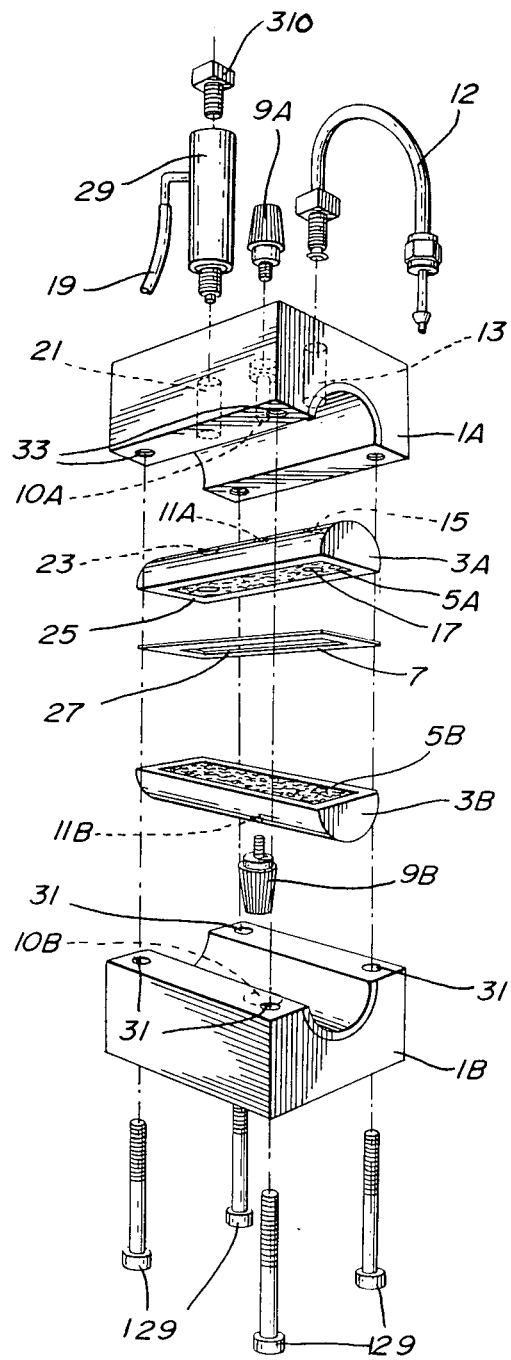

DUAL WORKING-ELECTRODE ELECTROCHEMICAL DETECTOR FOR HIGH PERFORMANCE LIQUID CHROMATOGRAPHY

BACKGROUND OF INVENTION (a) Field of the Invention

The invention relates to a dual working-electrode electrochemical detector. More specifically, the invention relates to such a detector wherein the working-electrodes are disposed in parallel, opposed, closely spaced, relationship.

(b) Description of Prior Art

High Pressure Liquid Chromatography (HPLC) has demonstrated a useful ability to separate large numbers of biologically active compounds in determining measurements of drugs and biochemical concentrations in biological fluids. Electrochemical cells have proven to be both sensitive and selective detectors for HPLC. The cells will typically include a single electrode, however, it has been shown that both the sensitivity and selectivity of the devices can be improved by using more than one working electrode. G. W. Schieffer, Anal. Chem., 52 (1980) 1944, W. A. MacCrehan and R. A. Durst, Anal. Chem., 53 (1981) 1700, D. A. Roston and P. T. Kissinger, Anal. Chem., 54 (1982) 429, and M. Goto, T. Nakamura and D. Ishii, J. Chromatogr., 226 (1981) 33. In the commonest of these arrangements, the cells include an upstream electrode to remove interfering species and a second electrode for the actual measurement.

Work has also been directed toward lowering the detection limits of electrochemical detectors by locating two working-electrodes on opposite walls of a thin layer cell. S. G. Weber, Ph.D. Thesis, McGill University, Montreal, 1979. This concept was first developed by Reilley and co-workers for stationary solutions, L. B. Anderson and C. N. Reilley, J. Electroanal. Chem., 10 (1965) 295. L. B. Anderson, C. N. Reilley, J. Electroanal. Chem., 10 (1965) 538. L. B. Anderson, B. McDuffie and C. N. Reilley, J. Electroanal. Chem., 12 (1966) 477 and C. N. Reilley, Pure Appl. Chem., 18 (1968) 137. Fenn et al extended this to flowing streams with only limited success. R. J. Fenn, S. Siggia and D. J. Curran, Anal. Chem., 50 (1978) 1067. For a discussion of the results of this see also Daryl A. Roston, Ronald E. Shoup and Peter T. Kissinger, Anal. Chem., 54 (1982) 1417 at page 1434 which also describes the redox (reduction-oxidation) cycling using parallel-opposed dual-electrodes. As can be seen in Roston et al, the Reilley et al results are not described as too promising.

SUMMARY OF INVENTION

It is an object of the invention to provide a dual working-electrode electrochemical detector having parallel, opposed, electrodes, which overcomes the difficulties of the prior art. In accordance with the invention, the electrodes are closely spaced so as to permit a substantial number of redox cycles along the lengths of the electrodes.

Further in accordance with the invention, the working-electrodes are separately controllable so that one of the electrodes will be at a reduction potential and the other of the electrodes will be at an oxidation potential.

Still further in accordance with the invention, the electrodes are made of a low temperature isotropic carbon (LTIC) material.

In accordance with a particular embodiment of the invention there is provided a dual working-electrode electrochemical detector for measuring characteristics of a biological fluid. The detector includes a first working electrode, a second working electrode, and means or holding the two electrodes in close, opposed, parallel relationship. Spacer means are disposed between the first and second electrodes for maintaining the electrodes in spaced relationship, and a channel for the flow of the fluid is formed between the electrodes. Feed means feed fluid to one end of the channel, and retrieval means retrieve fluid from the other end of the channel. Potentials applied to the electrodes are separately controllable whereby the electrodes can be held at different potentials.

BRIEF DESCRIPTION OF DRAWING

The invention will be better understood by an examination of the following description, together with the accompanying drawing which is an exploded view of a particular embodiment of the invention.

DESCRIPTION OF PREFERRED EMBODIMENTS

Referring to the drawing, the detector in accordance with the invention comprises means for holding the electrodes closely together comprising a pair of yokes 1A and 1B and hollow member electrode holders, illustrated in the drawing as hollow hemicylinders 3A and 3B. As can be seen, one side of the hollow hemicylinders is open and the open side of the hemicylinder is covered, respectively, by electrodes 5A and 5B. The electrodes comprise a material which can be worked flat to a high degree of precision as, for example, by optical polishing. Preferably, the electrodes comprise a low temperature isotropic carbon (LTIC).

Disposed between the electrodes, for maintaining the electrodes in spaced relationship, is a spacer means 7. The spacer means comprises as insulating material as, for example, Teflon or polyethylene.

Electrical connectors 9A and 9B extend, respectively, through openings 10A and 10B in yokes 1A and 1B, and through aligned openings 11A and 11B in hemicylinders 3A and 3B, to contact, respectively, electrodes 5A and 5B. As there are separate electrical connectors, the electrodes are separately controllable and can therefore be held at different potentials. Preferably, one of the electrodes is held at the reduction potential, and the other electrode is held at the oxidation potential, of the biological fluid being tested.

One end of pipe 12 is connected to a source of the biological fluid, and the other end of pipe 12 extends through a central opening in yoke 1A shown in dotted lines at 13. The opening 13 is aligned with opening 15 in hemicylinder 3A, and the opening 15 is, in turn, aligned with opening 17 in electrode 5A. The pipe 12 extending through the yoke 1A, the hemicylinder 3A and the opening 17, comprises the biological fluid feed means.

The biological fluid is retrieved through pipe means 19 whose inner end extends through central opening 21 in yoke 1A, aligned opening 23 in hemicylinder 3A, and opening 25 in electrode 5A.

A channel 27 is formed in the spacer 7, and the biological fluid flows in the channel 27. As can be seen, the feed means enters the channel at one end thereof, and the retrieval means enters the channel at the other end thereof.

The other end of the retrieval means also comprises an auxiliary electrode 29. The electrode 29 also forms a chamber, and reference electrode 310 extends through the chamber and, ultimately, through the opening 25 in electrode 5A and into the channel 27 as does also the auxiliary electrode 29. The electrodes 29 and 310 are, of course, spaced from each other and from the electrodes 5A and 5B.

Screws 129 extend through respective openings 31 and 33 in yokes 1A and 1B whereby the electrodes are held closely together in a leak-proof arrangement. At the same time, the electrodes are spaced from each other by the spacer 7.

In operation, biological fluid is fed, via pipe 12, to the channel 27, and is subsequently retrieved, at the other end of the channel, through the retrieval means including the pipe 19. Pumping arrangements, as is well known in the art, are provided for this purpose.

As the biological fluid flows through the channel, it undergoes redox cycling as explained in the Roston et al article above-referred to.

In an experimental arrangement, two LTIC plates, 2×6 cm, were glued with epoxy resin to two hemicylinders of Kel-F. Entrance and exit ports were then drilled through both the yoke 1A and the Kel-F block 3A.

As can be seen, the electrodes were glued to the open side of the Kel-F hemicylinders.

As is apparent, the area and thickness of the cell is determined by the channel cut 27. Although this design has the disadvantage of reducing one electrode area relative to another (because of the openings 17 and 25 in the electrode 5A) and of preventing the development of laminar flow before the stream reaches the electrode surface, these disadvantages are balanced by the achievement of a thin cell which does not leak and one in which the electrodes do not make contact with one another.

It was found that the most efficient channel shape is a rectangle. In the described embodiment, the channel is four centimeters long and one millimeter wide which yields a cell volume of 1 $\mu$l if 25-$\mu$m thick Teflon is used, or 0.5 $\mu$l if 12-$\mu$m thick Teflon is used. A particular circuit which can be used for independent control of the potentials of the two electrodes is described in S. A. McClintock and W. C. Purdy, Anal. Lett., 14 (1981) 791. To this biopotentiostat was added a difference circuit to obtain the sum of the oxidation and reduction currents. The signal was then filtered with a low pass filter with a variable time constant to reduce unwanted noise frequencies generated in the subtraction process. The difference circuit was constructed from three TL-071 operational amplifiers (Texas Instruments Inc., Dallas, TX) and the current-sampling circuit was constructed from an analog switch (AD-7512) controlled by a 555 timer. The frequency and duty cycle of the timer were established with external resistors and capacitors.

The flow system was constructed from an M6000-A pump (Waters Associates, Milford, MA) or a Varian 4100 pump (Varian Associates, Palo Alto, CA), an injection valve (Valco Instrument Co., Houston, TX) with a 10-$\mu$l sample loop for sample introduction and three Heath-Schlumberger Model SR-204 recorders (Heath Co., Mississauga, ONT., Canada). For chromatography, a 15-cm column was packed with 5-$\mu$m Spherisorb (CSC Inc., Town of Mount Royal, P.Q., Canada).

Although a particular embodiment has been described, this was for the purpose of illustrating, but not limiting, the invention. Various modifications, which will come readily to the mind of one skilled in the art, are within the scope of the invention as defined in the appended claims.

We claim:

1. A dual working-electrode electrochemical detector for measuring characteristics of a biological fluid, comprising:

a first working electrode;

a second working electrode;

means for holding the two electrodes in close, opposed parallel relationship;

spacer means between said first and second electrodes for maintaining said electrodes in spaced relationship;

means forming a channel for the flow of said fluid between said electrodes;

feed means for feeding fluid to one end of said channel; and retrieval means for retrieving fluid from the other end of said channel;

potentials applied to said electrodes being separately controllable whereby said electrodes can be held at different potentials;

wherein said means for holding said electrode comprises a first hollow member having an open side, said first electrode covering said open side of said first hollow member;

a first opening extending through said first hollow member to one end of said channel;

a second opening extending through said first hollow member to the other end of said channel;

a first opening in said first electrode being aligned with said first opening in said first hollow member;

a second opening in said electrode being aligned with said second opening in said first hollow member;

feed means being attached to said first opening in said first hollow member and extending to said one end of said channel;

retrieval means being attached to said second opening in said first hollow member and extending to said other end of said channel;

whereby fluid is fed to said one end of said channel and retrieved at the other end thereof;

and including a second hollow member with an open side, said second electrode covering said open side of said second hollow member; and means for holding said first and second hollow members in fluid-tight engagement with said first and second electrodes facing each other;

wherein said means for holding comprises a first yoke disposed over said first hollow member and a second yoke disposed over said second hollow member;

said first yoke having a first opening aligned with the first opening of said first hollow member and a second opening aligned with the second opening in said first hollow member.

2. A detector as defined in claim 1 wherein said channel is formed in said spacer means.

3. A detector as defined in claim 1 wherein said electrodes comprise a low temperature isotropic carbon.

4. A detector as defined in claim 3 and further including an auxiliary electrode and a reference electrode, said auxiliary and reference electrodes extending through said second opening in said first yoke, said second opening in said first hollow member, and said second opening in said first electrode, whereby to extend into said channel;

said auxiliary electrode being spaced from said reference electrode, and said reference electrode being spaced from said first and second working-electrodes.

5. A detector as defined in claim 4 wherein said feed means comprises pipe means and wherein said retrieval means comprises pipe means.

6. A detector as defined in claim 5 and including means for urging said yoke means towards each other whereby to maintain said detector in fluid-tight engagement.

* * * * *